United States Patent
Motai

(10) Patent No.: US 11,006,973 B2
(45) Date of Patent: May 18, 2021

(54) METHOD FOR CONSTRICTING TISSUE

(71) Applicant: OLYMPUS CORPORATION, Tokyo (JP)

(72) Inventor: Kosuke Motai, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 262 days.

(21) Appl. No.: 16/250,067

(22) Filed: Jan. 17, 2019

(65) Prior Publication Data
US 2020/0229841 A1    Jul. 23, 2020

(51) Int. Cl.
*A61B 17/3205*    (2006.01)
*A61B 17/221*    (2006.01)
*A61B 17/29*    (2006.01)

(52) U.S. Cl.
CPC ...... *A61B 17/32056* (2013.01); *A61B 17/221* (2013.01); *A61B 17/29* (2013.01); *A61B 2017/2212* (2013.01); *A61B 2017/2926* (2013.01)

(58) Field of Classification Search
CPC ... A61B 17/3205; A61B 17/221; A61B 17/29; A61B 17/32056; A61B 2017/00269; A61B 2017/22034; A61B 2017/2212; A61B 2017/2926
See application file for complete search history.

(56) References Cited

U.S. PATENT DOCUMENTS

| | | | |
|---|---|---|---|
| 6,352,503 B1 | 3/2002 | Matsui et al. | |
| 2009/0024138 A1* | 1/2009 | Saleh | A61B 17/32056 606/113 |
| 2014/0378988 A1* | 12/2014 | Raybin | A61B 17/221 606/113 |
| 2016/0278797 A1* | 9/2016 | Rohan | A61B 17/221 |
| 2016/0346002 A1* | 12/2016 | Avneri | A61B 17/32056 |
| 2016/0354070 A1* | 12/2016 | Motai | A61B 18/1477 |
| 2017/0000506 A1* | 1/2017 | Chu | A61B 17/221 |
| 2017/0049472 A1* | 2/2017 | Uihlein | A61B 17/221 |
| 2017/0156745 A1* | 6/2017 | Okada | A61B 17/221 |
| 2018/0028219 A1* | 2/2018 | Folan | A61B 17/32056 |

(Continued)

FOREIGN PATENT DOCUMENTS

JP    2000-37348 A    2/2000

OTHER PUBLICATIONS

"Hybrid ESD against colon tumor", Gastrointestinal tract Research Department, Hiroshima University, Retrieved from the Internet, URL: https://home.hiroshima-u.ac.jp/gitract/clinic_research/therapy.html, together with English machine translation.

*Primary Examiner* — George J Ulsh
(74) *Attorney, Agent, or Firm* — Scully, Scott, Murphy & Presser, P.C.

(57) ABSTRACT

In a tissue binding method, a ring-shaped part (15) of a snare wire (10b) is disposed at a position surrounding a binding target site, the tissue at the binding target site is pulled while the ring-shaped part (15) is pressed against the tissue around the binding target site at a plurality of pressing points that are located away from each other in the circumferential direction of the ring-shaped part (15), and, in a state in which the tissue at the binding target site is pulled, the diameter of the ring-shaped part (15) is reduced to bind the tissue, while adjusting the position in the pressing direction at one or more of the pressing points.

9 Claims, 9 Drawing Sheets

(56) References Cited

U.S. PATENT DOCUMENTS

| | | | |
|---|---|---|---|
| 2018/0325538 A1* | 11/2018 | Ambroze | A61B 17/22031 |
| 2020/0046400 A1* | 2/2020 | Sato | A61B 17/320016 |
| 2020/0178989 A1* | 6/2020 | Avneri | A61B 17/221 |
| 2020/0359878 A1* | 11/2020 | Schwarz | A61B 1/00158 |
| 2020/0360032 A1* | 11/2020 | Smith | A61B 17/221 |

* cited by examiner

METHOD FOR CONSTRICTING TISSUE

TECHNICAL FIELD

The present invention relates to a tissue binding method.

BACKGROUND ART

In a known tissue binding method, a snare wire is fixed around a binding target site with a plurality of clips, tissue at the binding target site surrounded by the snare wire is gripped and lifted, and in this state, the tissue is bound with the snare wire (for example, see Patent Literature 1).

With the method in Patent Literature 1, because the snare wire is fixed around the binding target site with the clips before the tissue at the binding target site is lifted, if the snare wire is not located at the position intended by an operator when the tissue is lifted, it is necessary to remove the clips, to shift the position of the snare wire, and to attach the clips again.

CITATION LIST

Patent Literature

{PTL 1} Japanese Unexamined Patent Application Publication No. 2000-37348

SUMMARY OF INVENTION

An aspect of the present invention is a tissue binding method including: disposing a ring-shaped snare wire at a position surrounding a binding target site; pulling tissue at the binding target site while pressing the snare wire against tissue around the binding target site at a plurality of positions that are located away from each other along the axis of the snare wire; and, in a state in which the tissue is pulled, reducing the diameter of the snare wire to bind the tissue, while adjusting the pressing position at one or more of the plurality of pressing points at which the snare wire is pressed against the tissue.

DESCRIPTION OF EMBODIMENTS

A tissue binding method according to an embodiment of the present invention will be described below with reference to the drawings.

Figure 4:
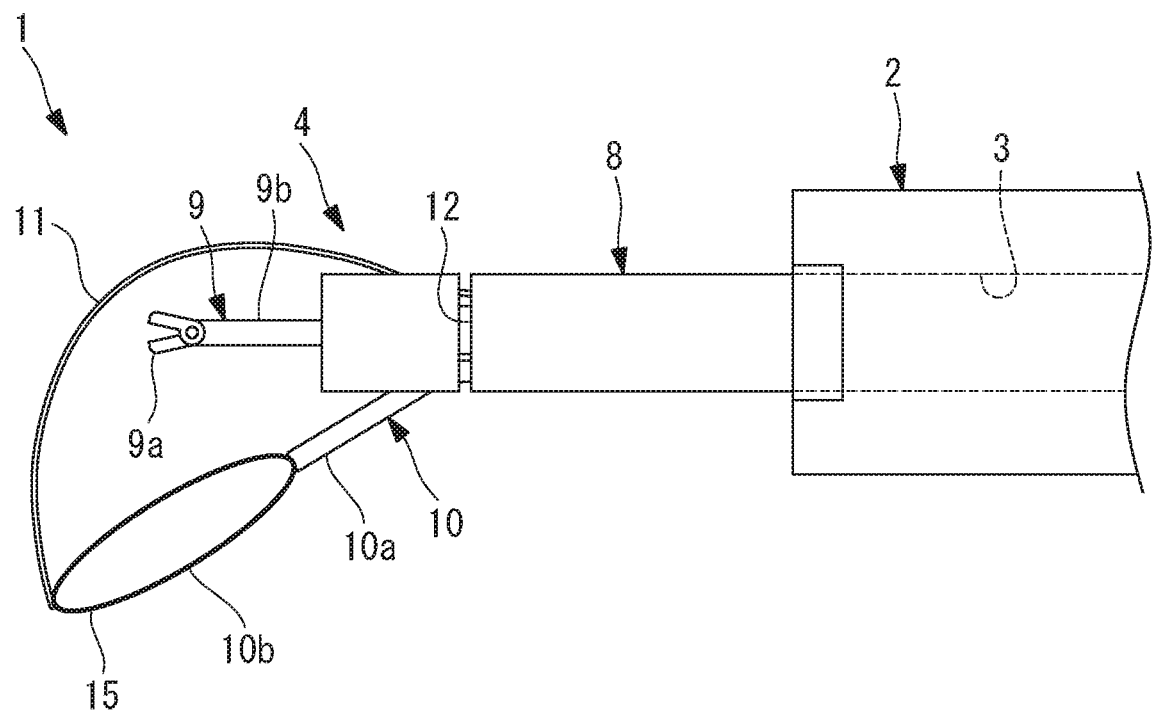
FIG. 4 is a side view of the medical apparatus showing a state in which, from the state in FIG. 3, the snare sheath, the pressing member, and a gripping forceps are further advanced.

The tissue binding method according to this embodiment is implemented by using a medical apparatus 1 shown in FIG. 4.

The medical apparatus 1 includes an endoscope 2 and a binding device 4 that is inserted through a channel 3 in the endoscope 2 so as to be capable of advancing and retracting.

Figure 1:
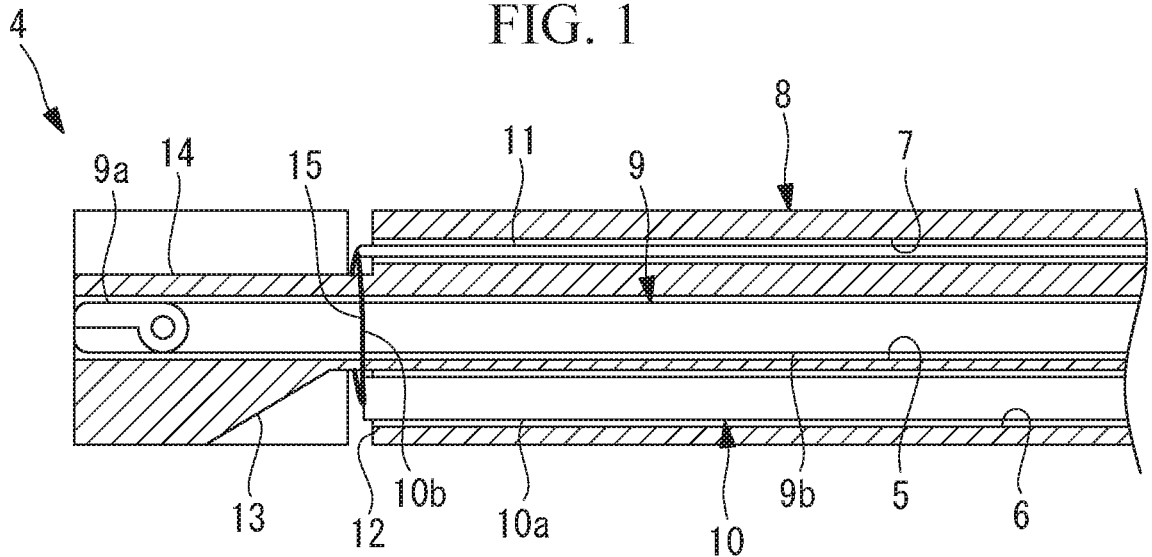
FIG. 1 is a vertical cross section showing a binding device of a medical apparatus used in a tissue binding method according to an embodiment of the present invention.

As shown in FIG. 1, the binding device 4 includes: a flexible sheath 8 having three independent lumens 5, 6 and 7 extending in the longitudinal direction; gripping forceps 9 inserted through the first lumen 5, which is located in the middle, so as to be capable of advancing and retracting; a snare 10 inserted through the second lumen 6, which is located on the radially outer side of the first lumen 5, so as to be capable of advancing and retracting; and a long pressing member 11 that is inserted through the third lumen 7, which is located on the opposite side of the first lumen 5 from the second lumen 6, so as to be capable of advancing and retracting.

The sheath 8 has a slit 12 formed over the entire circumference thereof, at a position a predetermined distance away from the distal end toward the base-end side. The slit 12 extends in the radial direction from the outer circumference of the sheath 8 to a depth reaching the second lumen 6 and the third lumen 7.

Figure 2:
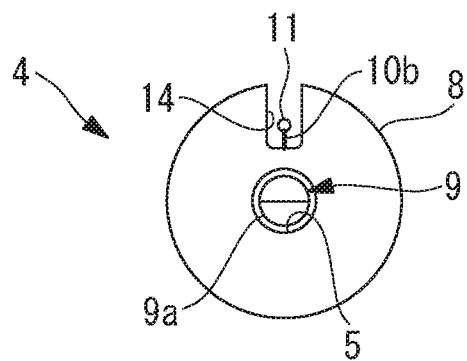
FIG. 2 is a front view of the binding device in FIG. 1.

As shown in FIG. 1, at a position corresponding to the second lumen 6, a slope 13 extending radially outward toward the distal end is provided. Furthermore, as shown in FIGS. 1 and 2, at a position corresponding to the third lumen 7, a cut-away portion 14 extending from the radially outer side of the third lumen 7 to the outer circumferential surface of the sheath 8 is provided.

Figure 3:
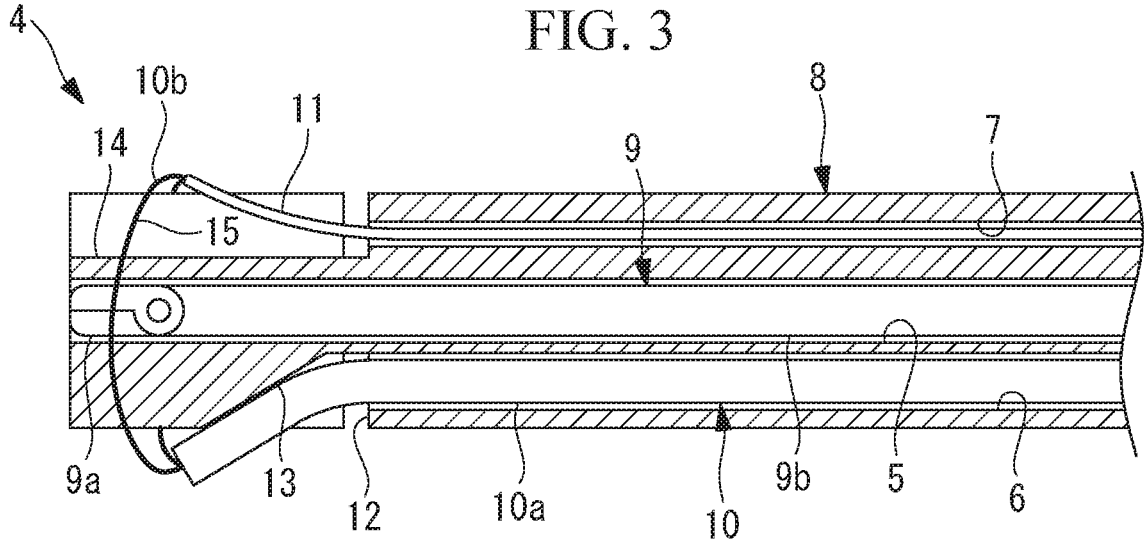
FIG. 3 is a vertical cross section showing a state in which a snare sheath and a pressing member start to be advanced from the binding device in FIG. 1.

As shown in FIG. 3, as a result of a portion of the snare 10, which is advanced through the second lumen 6 toward the distal end, said portion being located closer to the distal end than the slit 12 is, sliding on the slope 13, the distal end of a snare sheath 10a of the snare 10 is oriented radially outward.

A portion of the pressing member 11, which is advanced through the third lumen 7 toward the distal end, said portion being located closer to the distal end than the slit 12 is, can project also radially outward through the cut-away portion 14.

The gripping forceps 9 includes a flexible elongated portion 9b and a gripping part 9a that is provided at the distal end of the elongated portion 9b and that is capable of opening and closing. By manipulating a manipulating part (not shown) provided on the base-end side of the elongated portion 9b and outside the body, it is possible to open and close the gripping part 9a to grip a lesion X or to perform other operations.

The snare 10 includes a snare wire 10b disposed through the long, flexible, tubular snare sheath 10a. The snare wire 10b has, at the distal end thereof, a ring-shaped part 15 whose diameter can be reduced by manipulating the base end of the snare wire 10b. The snare 10 can sinter the tissue in contact with the ring-shaped part 15 with a high-frequency current applied to the base end of the snare wire 10b.

Figure 5:
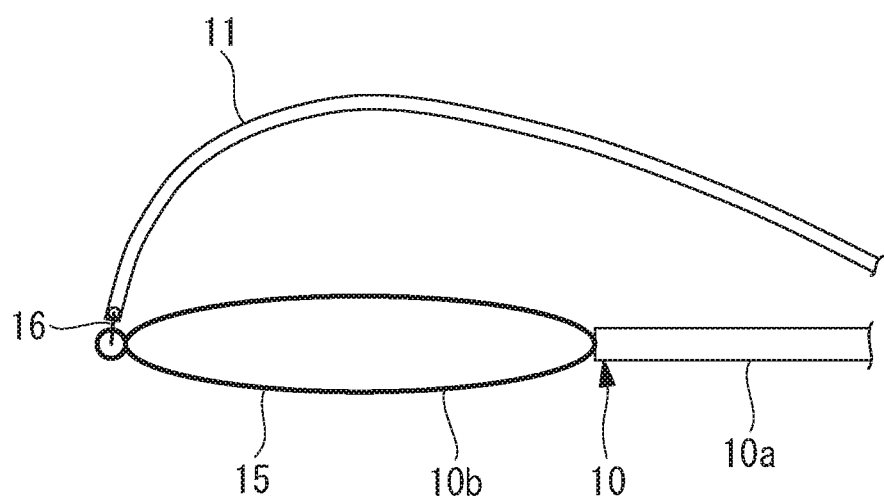
FIG. 5 is a diagram explaining a method for fixing the pressing member to a ring-shaped part of the snare wire of the binding device in FIG. 1.

The pressing member 11 is a long, flexible, wire-like member that can transmit a pressing force. As shown in FIG. 5, the distal end of the pressing member 11 is fixed to the ring-shaped part 15 of the snare 10 with a thread 16 that can be burnt by the high-frequency current supplied to the snare wire 10b. The fixing position is a predetermined distance away from the distal end of the snare sheath 10a along the axis of the snare wire 10b.

As shown in FIG. 1, in a state in which the distal end of the snare sheath 10a of the snare 10 and the distal end of the pressing member 11 are located at the position of the slit 12 in the sheath 8, the ring-shaped part 15 of the snare 10 is stored in the slit 12.

By pushing the snare 10 and the pressing member 11 toward the distal end, as shown in FIG. 4, the ring-shaped part 15 of the snare 10 is expanded in a ring shape, and the distal end of the snare sheath 10a and the distal end of the pressing member 11 are joined thereto at positions approximately 180° away from each other in the circumferential direction.

The tissue binding method according to this embodiment, using the binding device 4 of the thus-configured medical apparatus 1, will be described below with reference to the drawings.

Figure 6:
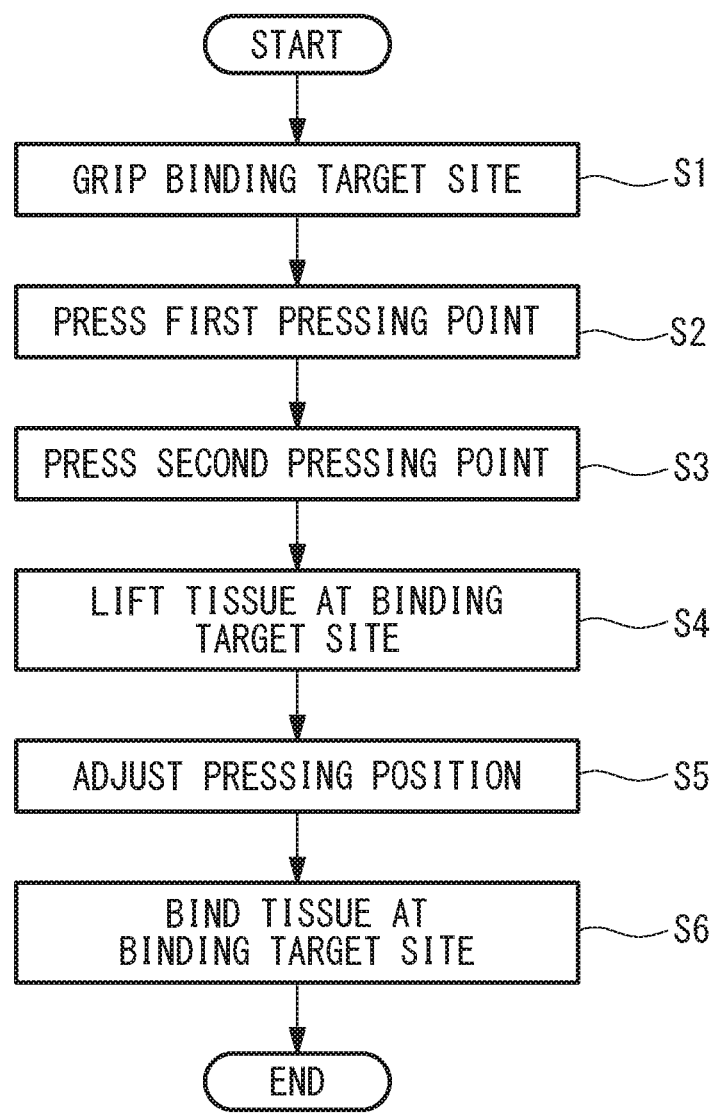
FIG. 6 is a flowchart explaining the tissue binding method according to the embodiment of the present invention.
Figure 7:
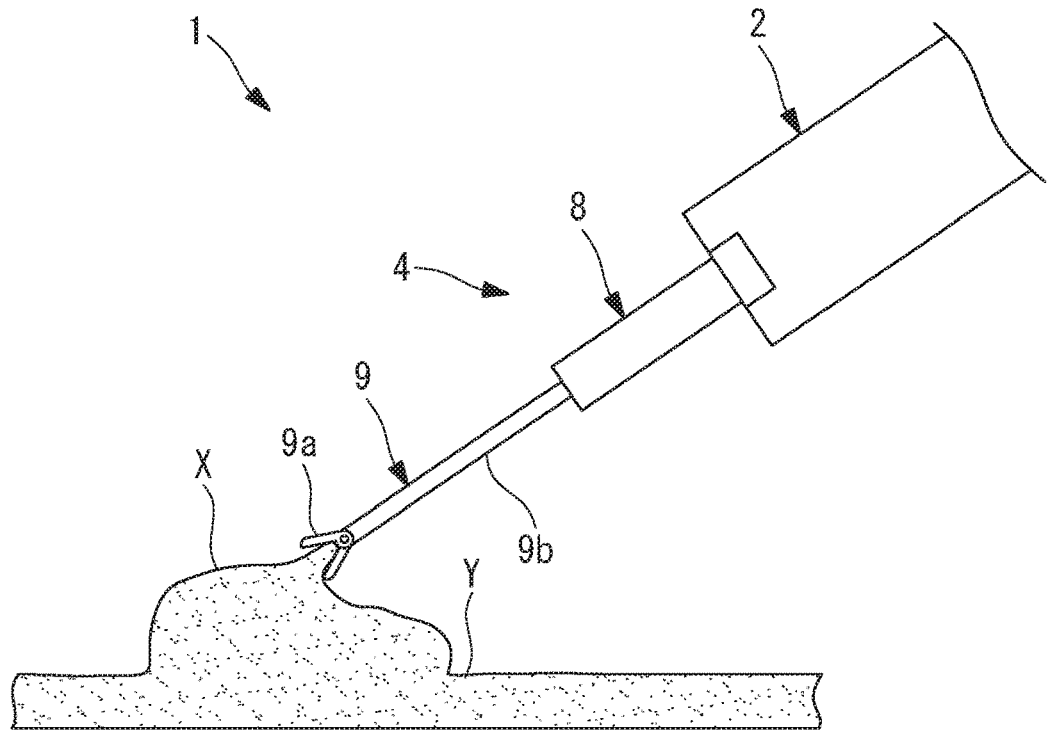
FIG. 7 is a diagram showing a state in which, in the tissue binding method in FIG. 6, tissue at the binding target site is gripped with the gripping forceps.

As shown in FIG. 6, in the tissue binding method according to this embodiment, first, the gripping forceps 9 stored in the first lumen 5 in the binding device 4 is advanced while a binding target site is being observed through the endoscope 2. Then, as shown in FIG. 7, the lesion X, which is the tissue at the binding target site, is gripped with the gripping part 9a provided at the distal end of the gripping forceps 9 (step S1).

Figure 8:
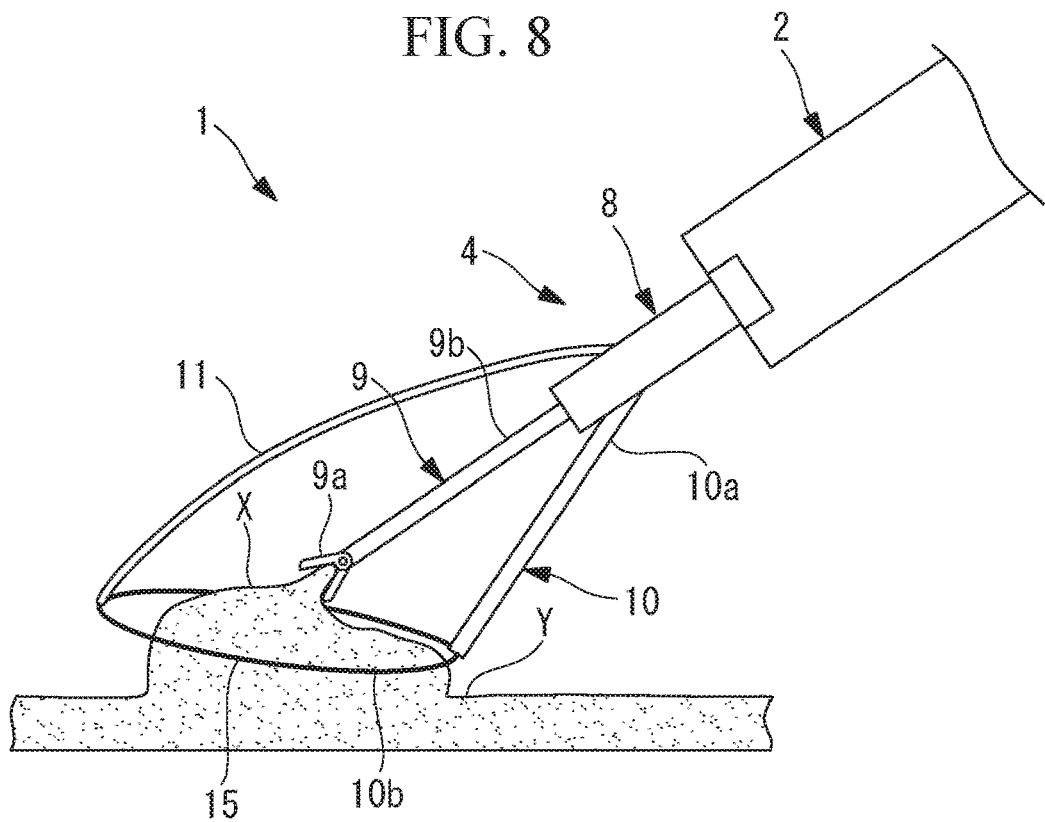
FIG. 8 is a diagram showing a state in which, in the state in FIG. 7, the ring-shaped part of the snare wire is disposed around the binding target site.
Figure 9:
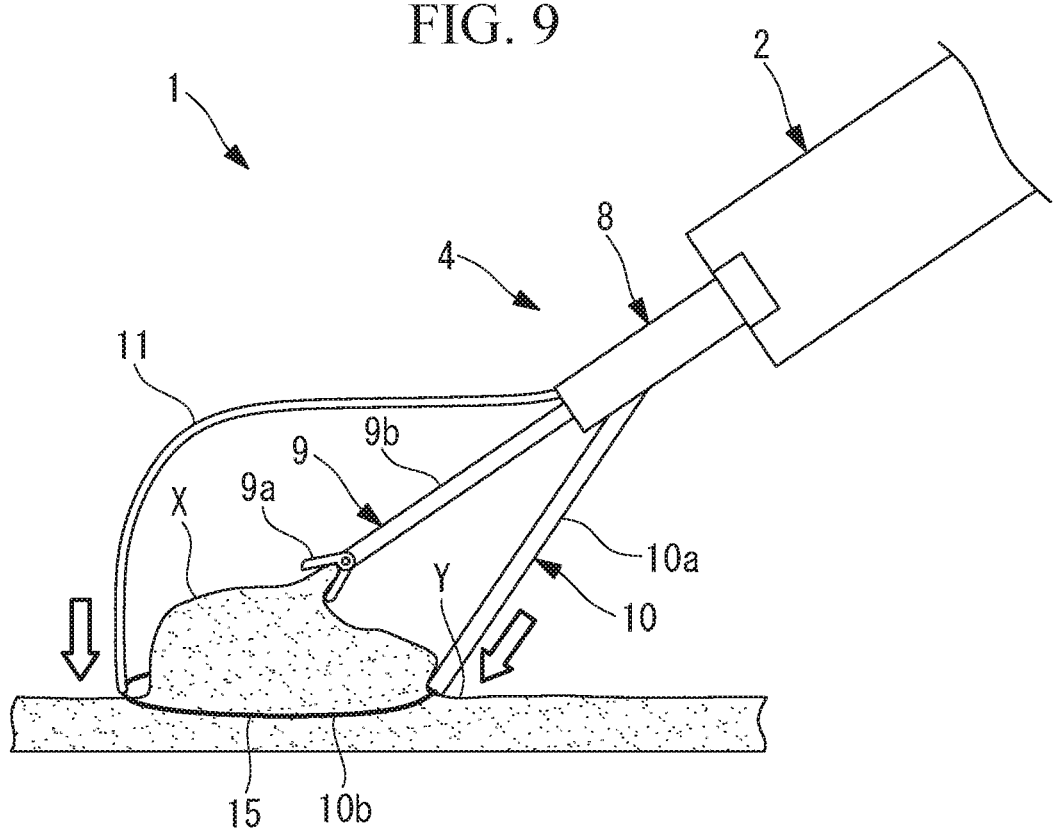
FIG. 9 is a diagram showing a state in which, in the state in FIG. 8, the snare wire is pressed against the tissue at a plurality of pressing points, with the distal end of the snare sheath and the distal end of the pressing member.

Next, as shown in FIG. 8, the snare 10 stored in the second lumen 6 in the binding device 4 and the pressing member 11 stored in the third lumen 7 are simultaneously advanced, thus widely expanding the ring-shaped part 15 of the snare 10. Then, as shown in FIG. 9, by manipulating the snare sheath 10a, the distal end of the snare sheath 10a is pressed against the tissue Y around the lesion X, at a desired first pressing point A around the binding target site (step S2). Subsequently, by manipulating the pressing member 11, the distal end of the pressing member 11 is pressed against the tissue Y around the lesion X, at a second pressing point B around the binding target site (step S3). As a result, the ring-shaped part 15 of the snare 10 is disposed at a position surrounding the binding target site.

Figure 10:
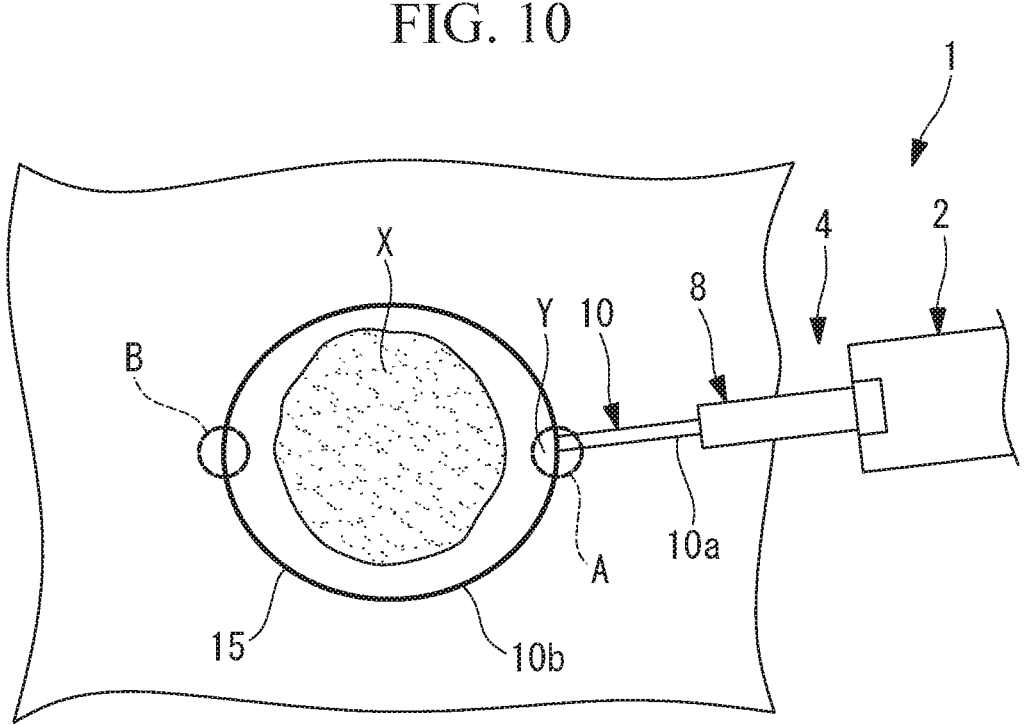
FIG. 10 is a plan view explaining the pressing points in FIG. 9.

As a result, the ring-shaped part 15 of the snare 10 is disposed at a position surrounding the lesion X, which is the tissue at the binding target site, and the ring-shaped part 15 of the snare 10 is pressed against the tissue Y around the binding target site with the distal end of the snare sheath 10a and the distal end of the pressing member 11. Specifically, as shown in FIG. 10, it is possible to press the ring-shaped part 15 against the tissue Y at two positions A and B located approximately 180° away from each other in the circumferential direction of the ring-shaped part 15 surrounding the binding target site.

Figure 11:
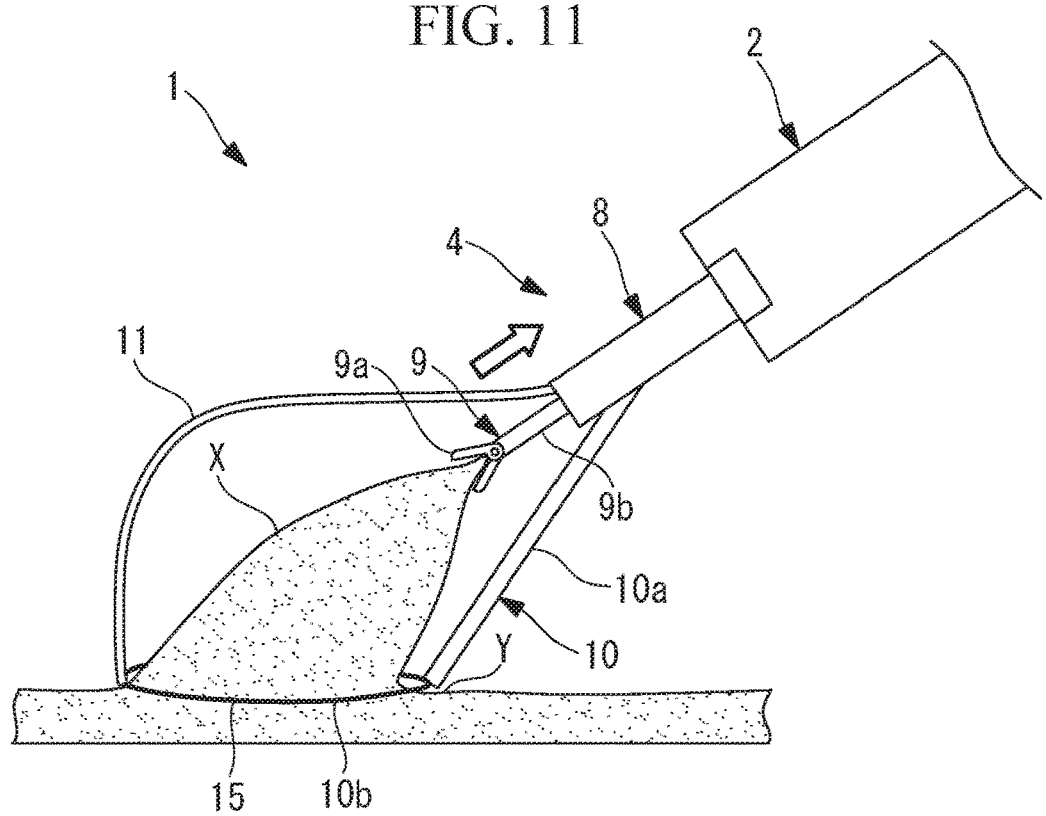
FIG. 11 is a diagram showing a state in which, from the state in FIG. 9, the gripping forceps is pulled to lift the tissue at the binding target site.

Then, as shown in FIG. 11, in a state in which the ring-shaped part 15 is pressed against the tissue Y, the gripping forceps 9 is pulled toward the base end, thus lifting the lesion X, which is the tissue at the binding target site, with the gripping forceps 9 (step S4).

Thereafter, the position of the ring-shaped part 15 with respect to the binding target site is checked through the endoscope 2, and, if the ring-shaped part 15 is displaced from the desired position, the pressing positions of the first pressing point A and the second pressing point B are adjusted by advancing or retracting the snare sheath 10a and the pressing member 11 (step S5).

Figure 12:
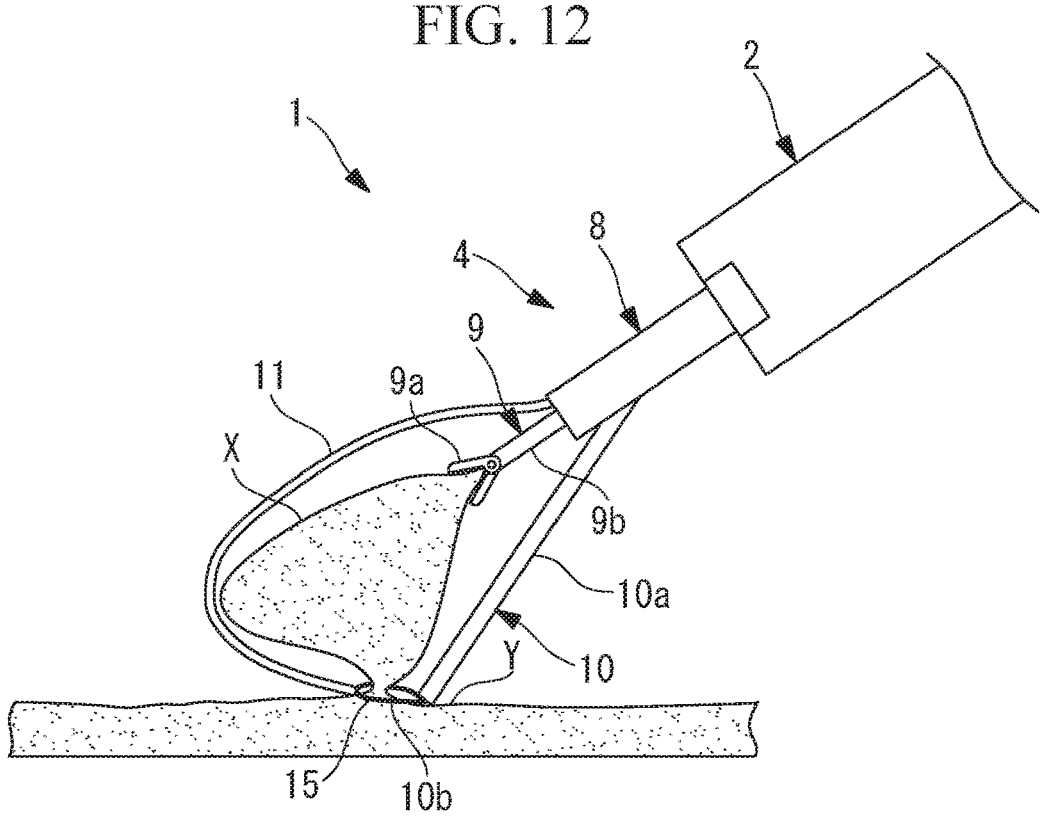
FIG. 12 is a diagram showing a state in which, in the state in FIG. 11, the ring-shaped part of the snare wire is narrowed to bind the tissue.

By pulling the base end of the snare wire 10b in a state in which the position of the ring-shaped part 15 of the snare wire 10b has been adjusted to the desired position, as shown in FIG. 12, the diameter of the ring-shaped part 15 is reduced to bind the lesion X, which is the tissue at the binding target site (step S6).

As described above, in the tissue binding method according to this embodiment, the ring-shaped part 15 of the snare wire 10b is disposed at a position surrounding the binding target site while the peripheral tissue Y including the lesion X, which is the tissue at the binding target site, is being observed through the endoscope 2, and the ring-shaped part 15 is pressed against the tissue Y at the two pressing points A and B that are located away from each other along the axis of the snare wire 10b. Hence, it is possible to move the ring-shaped part 15 in the direction toward the desired binding position, even in the case where the surface of the tissue Y is not flat.

By pulling the lesion X, which is the tissue at the binding target site, located inside the ring-shaped part 15 while pressing the ring-shaped part 15 against the peripheral tissue Y and then reducing the diameter of the ring-shaped part 15 while adjusting the position in the pressing direction at one or more of the pressing points A and B, an advantage is afforded in that it is possible to easily place the snare wire 10b at an intended position and to bind the desired site of the lesion X in a state in which the lesion X, which is the tissue at the binding target site, is lifted.

Figure 13:
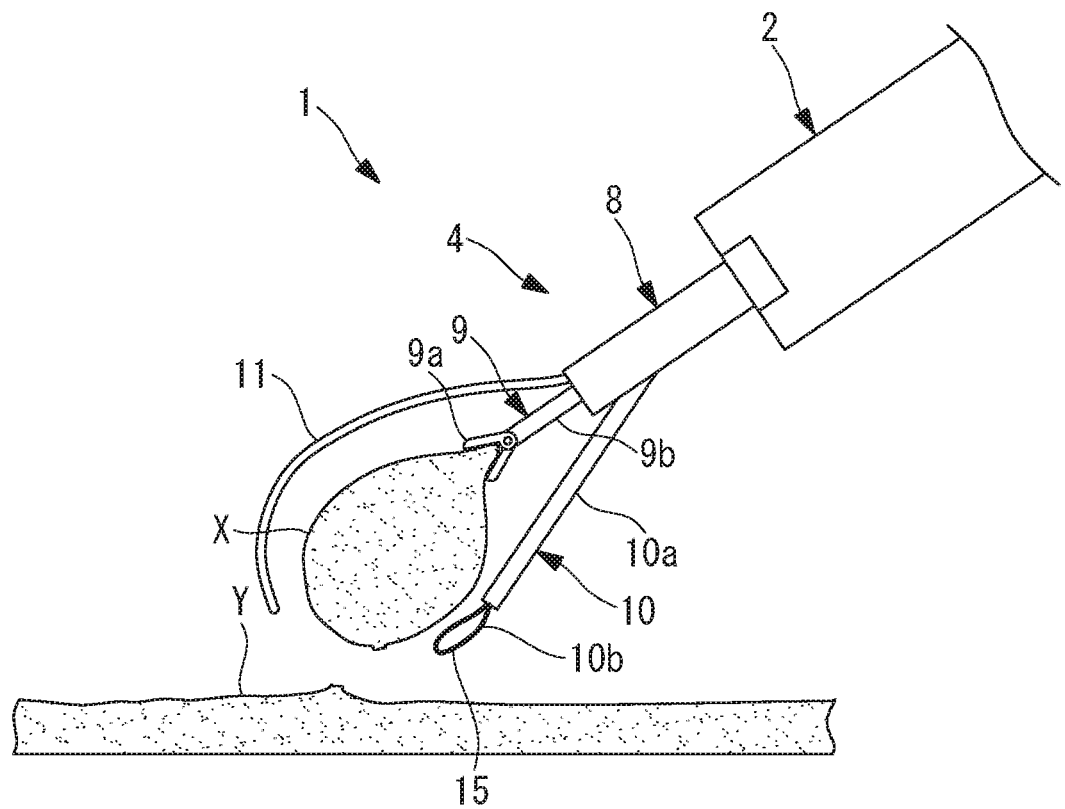
FIG. 13 is a diagram showing a state in which, in the state in FIG. 12, a high-frequency current is supplied to the snare wire to cut off the tissue.
Figure 14:
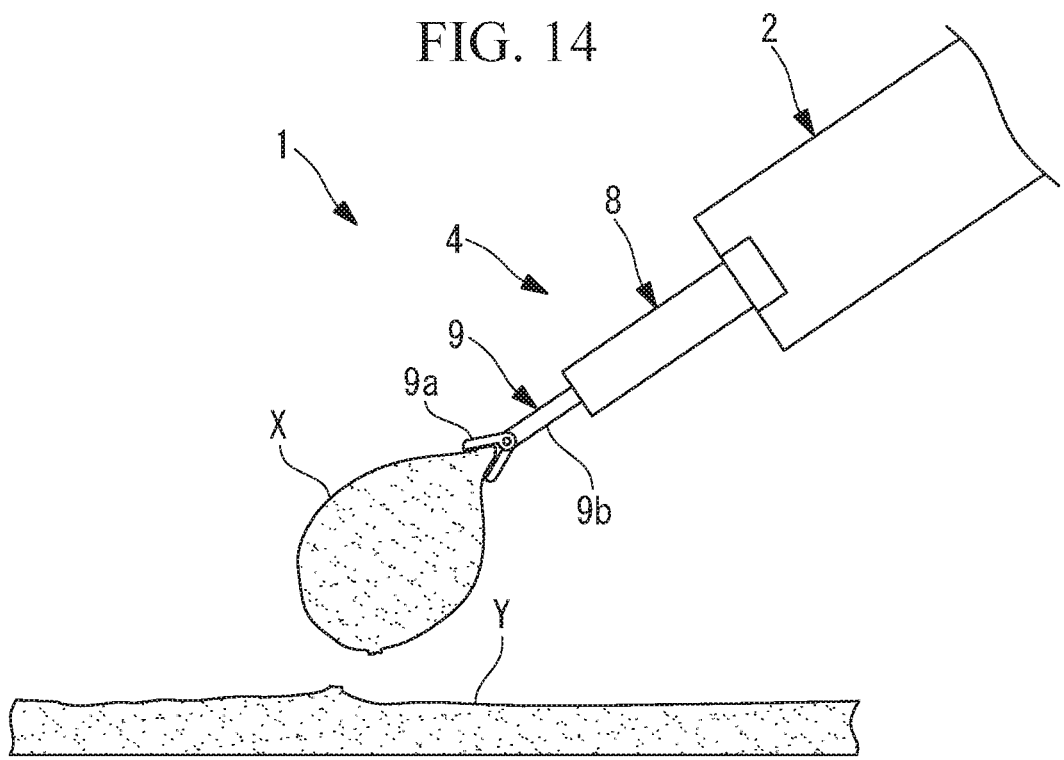
FIG. 14 is a diagram showing a state in which, from the state in FIG. 13, the snare and the pressing member are stored in the sheath.

In the tissue binding method according to this embodiment, by supplying a high-frequency current to the snare wire 10b in a state in which the lesion X, which is the tissue at the binding target site, is bound, as shown in FIG. 13, it is possible to sinter the lesion X at the binding position, and the thread 16 with which the pressing member 11 is fixed to the ring-shaped part 15 is cut. As a result, as shown in FIG. 14, it is possible to store the snare 10 in the second lumen 6 and to store the pressing member 11 in the third lumen 7, thus preventing the pressing member 11 and the snare 10 from serving as obstacles when the lesion X gripped with the gripping forceps 9 is collected from inside the body.

Figure 15:
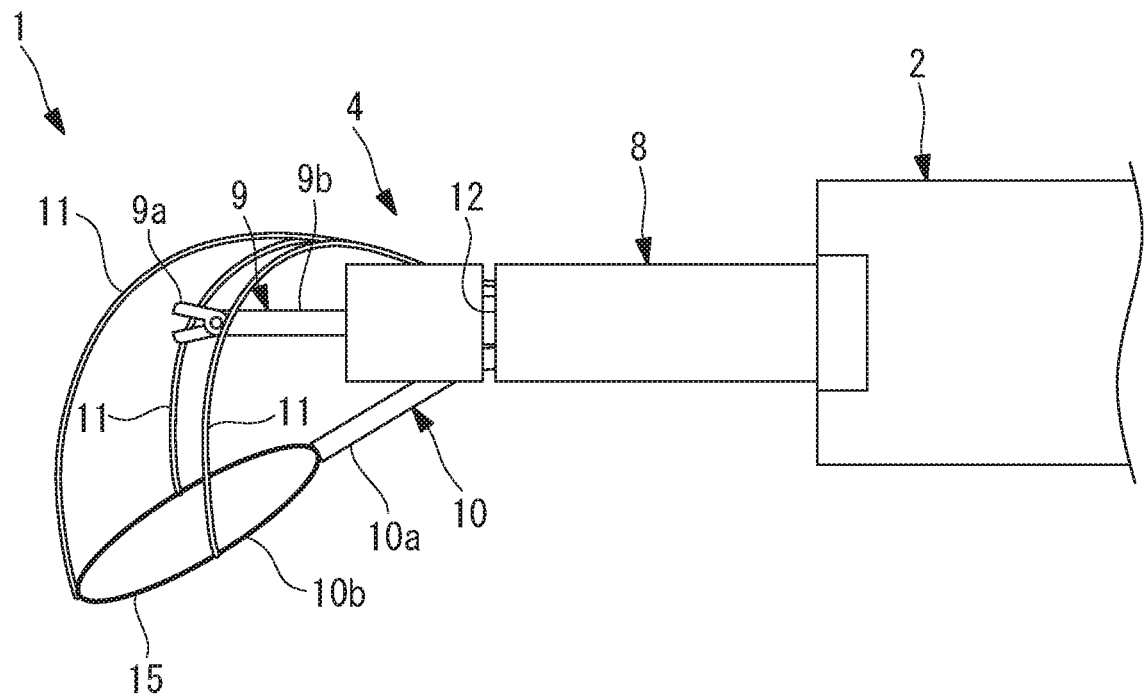
FIG. 15 is a diagram showing a modification of the medical apparatus in FIG. 4.
Figure 16:
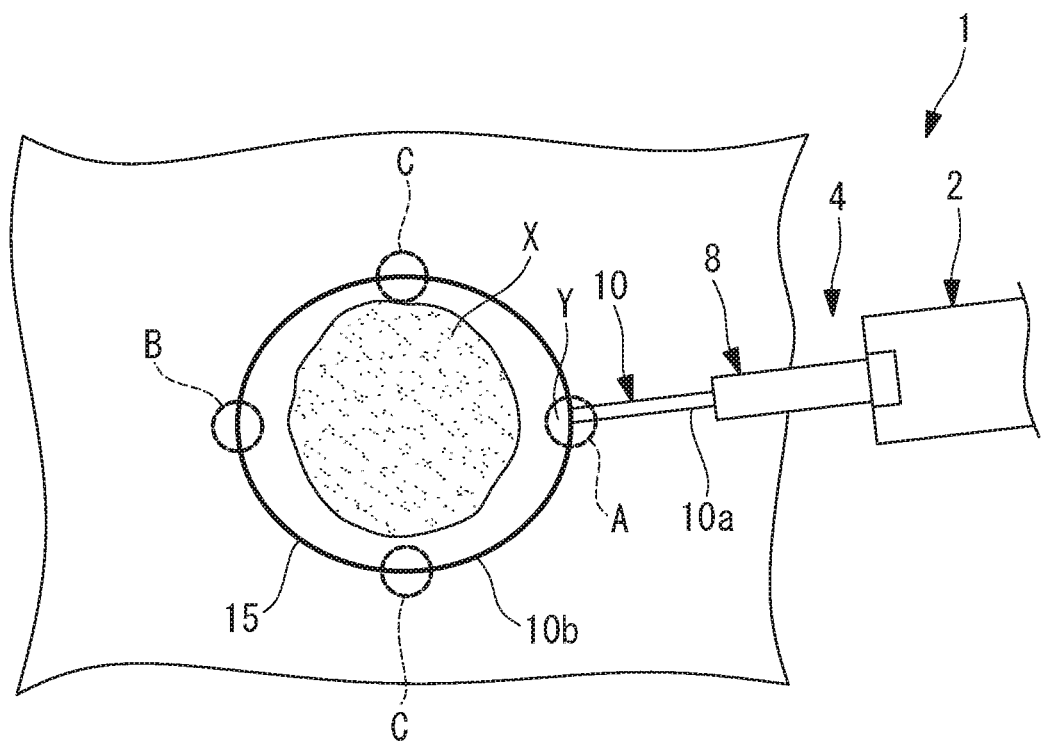
FIG. 16 is a plan view showing an example of pressing points at which the snare sheath and the pressing member of the medical apparatus in FIG. 15 press the ring-shaped part of the snare wire.

Furthermore, in this embodiment, although a single second pressing point B that is different from the first pressing point A, at which the ring-shaped part 15 is pressed by the snare sheath 10a, is pressed by the single pressing member 11, instead, as shown in FIGS. 15 and 16, the distal ends of a plurality of, for example, three, pressing members 11 that can be independently advanced and retracted may be fixed to the ring-shaped part 15 at positions approximately 90° away from each other along the axis of the snare wire 10b, so that the ring-shaped part 15 is pressed against the tissue Y at four pressing points (the first pressing point A, the second pressing point B, and the third pressing points C) including the first pressing point A pressed by the distal end of the snare sheath 10a. By doing so, it becomes easy to place the ring-shaped part 15 so as to conform to the irregular shape of the tissue Y, thus making it possible to bind the lesion X, which is the tissue at the binding target site, at the desired position.

Figure 17:
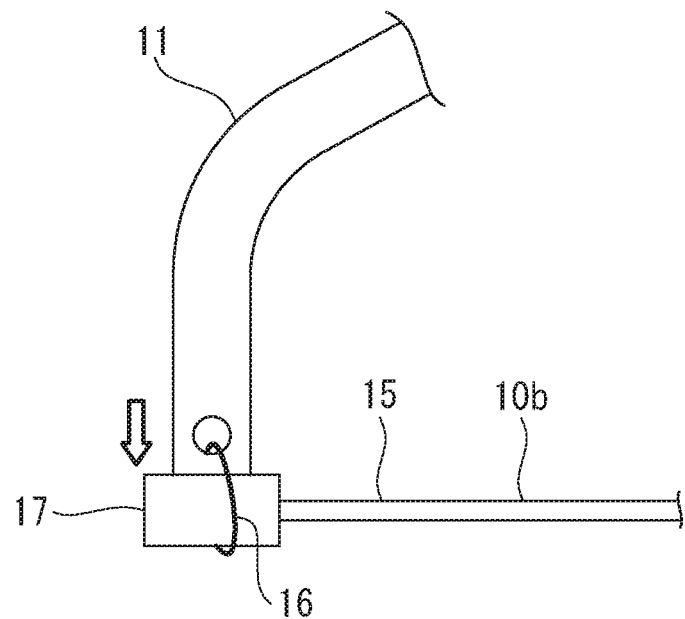
FIG. 17 is a diagram showing a modification of the method for fixing the pressing member to the snare wire in FIG. 5.

Furthermore, in this embodiment, although the distal end of the pressing member 11 is fixed to the ring-shaped part 15 of the snare wire 10b with a thread, as shown in FIG. 17, it is also possible to provide a receiving part 17, against which the distal end face of the pressing member 11 is pressed, on the snare wire 10b. The receiving part 17 may be formed by fixing a flat-plate-shaped member having a greater area than the wire diameters of the snare wire 10b and the pressing member 11 to the ring-shaped part 15 of the snare wire 10b. By doing so, it is possible to more reliably transmit, via the receiving part 17, the pressing force exerted by the pressing member 11 to the ring-shaped part 15 of the snare wire 10b.

Figure 18:
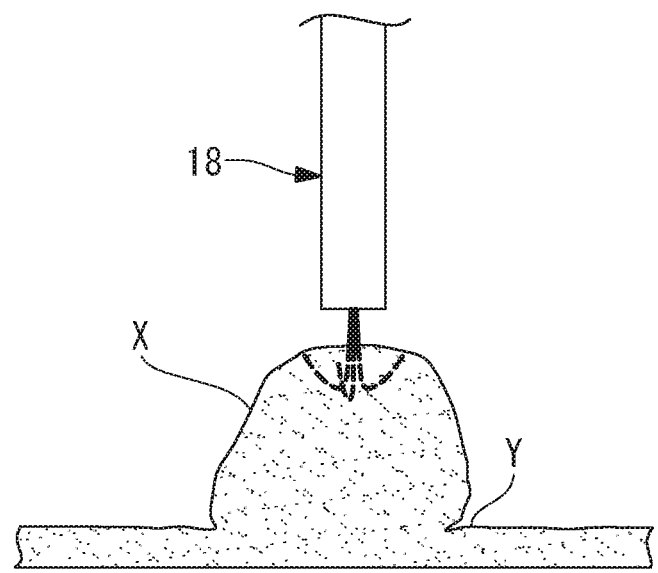
FIG. 18 is a diagram explaining an anchor member, which may be used instead of the gripping forceps of the binding device in FIG. 1.

Furthermore, in this embodiment, although the binding device 4 has the gripping forceps 9 that grip the lesion X, instead, as shown in FIG. 18, it is possible to employ an anchor member 18 that cannot be removed in a state stuck in the lesion X. With this configuration, by sticking the anchor member 18 in the lesion X, it is possible to more reliably prevent the lesion X from falling off and to more reliably hold the lesion X when the lesion X, which is the tissue at the binding target site, is lifted or when the lesion X that has been cut off is collected.

Furthermore, in this embodiment, although the pressing points A and B pressed by the distal end of the snare sheath 10a and the distal end of the pressing member 11 are adjusted by manipulating the snare sheath 10a and the pressing member 11 while being observed through the endoscope 2, instead, it is possible to adjust the pressing points A and B pressed by the distal end of the snare sheath 10a and the distal end of the pressing member 11, by advancing or retracting the endoscope 2 itself or by the bending action of a bending portion of the endoscope 2, while moving the field of view of the endoscope 2.

Alternatively, an upright base, which presses the sheath 8 in the radial direction, may be provided on the endoscope 2. By operating the upright base to change the projecting angle of the sheath 8 from the channel 3 in the endoscope 2, the pressing points A and B pressed by the distal end of the snare sheath 10a and the distal end of the pressing member 11 are adjusted.

In this embodiment, although it has been described that the binding device 4 includes the sheath 8 having three lumens 5, 6 and 7, instead, the sheath 8 does not need to be provided. In such a case, the gripping forceps 9, the snare 10, and the pressing member 11 may be directly inserted through the channel 3 in the endoscope 2.

The above-described embodiment is derived from the following aspects of the present invention.

An aspect of the present invention is a tissue binding method including: disposing a ring-shaped snare wire at a position surrounding a binding target site; pulling tissue at the binding target site while pressing the snare wire against tissue around the binding target site at a plurality of positions that are located away from each other along the axis of the snare wire; and, in a state in which the tissue is pulled, reducing the diameter of the snare wire to bind the tissue, while adjusting the pressing position at one or more of the plurality of pressing points at which the snare wire is pressed against the tissue.

According to this aspect, the ring-shaped snare wire is disposed at a position surrounding the binding target site while the peripheral tissue including the binding target site is observed through the endoscope, and the snare wire is pressed against the tissue at a plurality of positions that are located away from each other along the axis of the snare wire. Hence, even in the case where the surface of the tissue is not flat, it is possible to move the snare wire in the direction toward the desired binding position. By pulling the tissue at the binding target site located inside the snare wire while pressing the snare wire against the peripheral tissue and then reducing the diameter of the snare wire while adjusting the pressing position at one or more of the plurality of pressing points at which the snare wire is pressed against the tissue, it is possible to easily dispose the snare wire at an intended position and to bind the desired part of the tissue in a state in which the binding target site is lifted.

In the above-described aspect, the snare wire may be disposed so as to be capable of projecting from and retracting into the distal end of the snare sheath, the snare wire may be pressed against the tissue with the distal end of the snare sheath at the first pressing point of the plurality of pressing points, and the snare wire may be pressed against the tissue at a second pressing point of the plurality of pressing points that is different from the first pressing point, after the snare wire is pressed against the tissue at the first pressing point.

With this configuration, it is possible to easily adjust the pressing position at the second pressing point that is different from the first pressing point, after the first pressing point of the snare wire is pressed against the tissue by using the distal end of the snare sheath that supports the snare wire, thus positioning the snare wire respect to the binding target site.

Furthermore, in the above aspect, the pressing position may be adjusted also at a third pressing point of the plurality of pressing points that is different from the first pressing point or the second pressing point.

With this configuration, by adjusting the positions at the second pressing point and the third pressing point, it is possible to more reliably press the snare wire against tissue that is not flat.

Furthermore, in the above aspect, the distal end of a long pressing member that is advanced and retracted in the longitudinal direction to transmit a pressing force may be fixed to the second pressing point.

With this configuration, by advancing or retracting the long pressing member in the longitudinal direction, it is possible to transmit, with the distal end of the pressing member, a pressing force to the second pressing point.

Furthermore, in the above aspect, the snare sheath and the pressing member may be inserted through channels in an endoscope so as to be capable of projecting from and retracting into the distal end of the endoscope.

With this configuration, it is possible to manipulate the snare sheath and the pressing member on the outside of the body while observing the binding target site through the endoscope and to press the snare wire against the tissue at a plurality of positions with the distal end of the snare sheath and the distal end of the pressing member.

REFERENCE SIGNS LIST 2 endoscope
3 channel
10a snare sheath
10b snare wire
11 pressing member
A first pressing point (pressing point)
B second pressing point (pressing point)
C third pressing point (pressing point)
X lesion (tissue)
Y tissue

The invention claimed is:

1. A tissue binding method comprising:
gripping tissue at a binding target site with a gripping tool;
in a state in which the tissue at the binding target site is gripped with the gripping tool, disposing a snare wire at a position surrounding the binding target site, the snare wire being expanded in a loop shape from a distal end of a snare sheath;
pulling, with the gripping tool, the tissue at the binding target site;
concurrently with the pulling, pressing the snare wire against tissue around the binding target site at a first position corresponding to the distal end of the snare sheath and one or more second positions, the first position and the one or more second positions being located away from each other along a longitudinal axis of the snare wire; and
concurrently with the pulling and the pressing, reducing a size of the loop shape of the snare wire to bind the tissue at the binding target site, while adjusting at least one of the first position and the one or more second positions.

2. The tissue binding method according to claim 1, wherein the snare wire is pressed against the tissue around the binding target site at the or more second positions after the snare wire is pressed against the tissue around the binding target site at the first position.

3. The tissue binding method according to claim 2, wherein the pressing comprises advancing a distal end of one or more long pressing members towards the bending target site to transmit a pressing force to at least the one or more second positions.

4. The tissue binding method according to claim 3, further comprising inserting the snare sheath and the pressing member through channels in an endoscope so as to be capable of projecting from and retracting into a distal end of the endoscope.

5. The tissue binding method according to claim 1, further comprising connecting the distal end of the one or more pressing members to the snare wire at the one or more second positions.

6. The tissue binding method according to claim 5, further comprising, subsequent to the reducing:
excising the tissue binded at the binding target site; and
releasing the connection between the distal end of the one or more pressing members and the snare wire at the one or more second positions.

7. The tissue binding method according to claim 6, wherein the excising and the releasing comprise applying a high-frequency current to the snare wire.

8. The tissue binding method according to claim 5, further comprising, prior to the gripping, advancing a medical apparatus towards the binding target site while the one or more pressing members, the gripping tool and the snare sheath are disposed in one or more lumens in the medical apparatus and the snare wire is stored in a slot at a distal end of the medical apparatus.

9. The tissue binding method according to claim 8, wherein the expanding of the snare wire in the loop shape comprises advancing distal ends of the snare sheath and the one or more pressing members distally and radially outward from the distal end of the medical apparatus.

* * * * *